(12) United States Patent
Ganapathy et al.

(10) Patent No.: US 9,326,683 B2
(45) Date of Patent: May 3, 2016

(54) SYSTEMS AND METHODS FOR DETECTION OF WOUND FLUID BLOOD AND APPLICATION OF PHOTOTHERAPY IN CONJUNCTION WITH REDUCED PRESSURE WOUND TREATMENT SYSTEM

(75) Inventors: Premnarayan Ganapathy, Brookline, MA (US); Royce Johnson, Universal City, TX (US); Tim Robinson, Basingstok (GB); Christopher B. Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 1287 days.

(21) Appl. No.: 13/089,077

(22) Filed: Apr. 18, 2011

(65) Prior Publication Data

US 2011/0196284 A1 Aug. 11, 2011

Related U.S. Application Data

(63) Continuation of application No. 11/327,662, filed on Jan. 6, 2006, now Pat. No. 7,947,033, and a (Continued)

(51) Int. Cl.
*A61M 1/00* (2006.01)
*A61B 5/00* (2006.01)

(Continued)

(52) U.S. Cl.
CPC .............. *A61B 5/0059* (2013.01); *A61B 5/1468* (2013.01); *A61B 5/14542* (2013.01);

(Continued)

(58) Field of Classification Search
CPC ......... A61M 31/00; A61M 1/00; A61M 5/20; A61M 35/00; A61M 27/00; A61F 2/00; B65D 81/00
USPC .......................................... 604/327, 541, 543
See application file for complete search history.

(56) References Cited

U.S. PATENT DOCUMENTS 1,355,846 A 10/1920 Rannells
2,547,758 A 4/1951 Keeling (Continued)

FOREIGN PATENT DOCUMENTS

AU 550575 A1 8/1982
AU 745271 4/1999

(Continued)

OTHER PUBLICATIONS

Non-Final Office Action date mailed Dec. 12, 2001 for U.S. Appl. No. 09/544,399.

(Continued)

*Primary Examiner* — Tatyana Zalukaeva
*Assistant Examiner* — Ilya Treyger

(57) ABSTRACT

Wound fluid blood detection systems and methods are described that are operable in conjunction with reduced pressure wound treatment (RPWT) systems, as well as ancillary therapy and monitoring systems applied concurrently with RPWT systems. The blood detection monitor operates by optically characterizing the content of wound fluids to the extent of identifying percentage blood content. This identification relies upon the transmission of select wavelengths of light across a volume of wound fluid to a photo detector (connected to signal processing instrumentation) capable of quantifying the absorption characteristics of the fluid. The detection components may be implemented in conjunction with either a fluid flow conduit (i.e. the reduced pressure tubing directing fluid away from the wound dressing) or more directly in association with the materials that comprise the wound dressing positioned within the wound bed itself. In addition, the present invention is configured to operate in conjunction with blood gas monitoring, systems operating with the RPWT. Finally, the components of the systems that serve to illuminate the wound bed, lend themselves to use in conjunction with illumination in discreet electromagnetic wave wavelengths suitable for the application of phototherapy.

11 Claims, 4 Drawing Sheets

Related U.S. Application Data continuation of application No. 10/867,990, filed on Jun. 15, 2004, now Pat. No. 7,524,286, which is a continuation-in-part of application No. 10/085,321, filed on Feb. 28, 2002, now Pat. No. 6,856,821, which is a continuation-in-part of application No. 09/579,755, filed on May 26, 2000, now abandoned, said application No. 13/089,077 is a continuation-in-part of application No. 09/544,399, filed on Apr. 6, 2000, now Pat. No. 6,994,702, and a continuation-in-part of application No. 10/090,358, filed on Mar. 4, 2002, now Pat. No. 7,799,004.

(60) Provisional application No. 60/127,936, filed on Apr. 6, 1999, provisional application No. 60/273,587, filed on Mar. 5, 2001.

(51) Int. Cl.
*A61B 5/145* (2006.01)
*A61B 5/1468* (2006.01)
*A61M 31/00* (2006.01)
*A61M 5/20* (2006.01)
*A61M 35/00* (2006.01)
*A61M 27/00* (2006.01)
*A61F 2/00* (2006.01)
*B65D 81/00* (2006.01)
*A61N 5/06* (2006.01)

(52) U.S. Cl.
CPC .............. *A61B5/445* (2013.01); *A61B 5/6834* (2013.01); *A61M 1/0025* (2014.02); *A61M 1/0088* (2013.01); *A61N 2005/0651* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,702 A | 11/1990 | Anderson |
| 4,969,880 A | 11/1990 | Zamierowski |
| 4,985,019 A | 1/1991 | Michelson |
| 5,037,397 A | 8/1991 | Kalt et al. |
| 5,066,859 A | 11/1991 | Karkar et al. |
| 5,086,170 A | 2/1992 | Luheshi et al. |
| 5,092,858 A | 3/1992 | Benson et al. |
| 5,100,396 A | 3/1992 | Zamierowski |
| 5,100,429 A | 3/1992 | Sinofsky et al. |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,358,503 A | 10/1994 | Bertwell et al. |
| 5,437,622 A | 8/1995 | Carion |
| 5,437,651 A | 8/1995 | Todd et al. |
| 5,474,528 A | 12/1995 | Meserol |
| 5,527,293 A | 6/1996 | Zamierowski |
| 5,549,584 A | 8/1996 | Gross |
| 5,556,375 A | 9/1996 | Ewall |
| 5,584,296 A | 12/1996 | Cui et al. |
| 5,607,388 A | 3/1997 | Ewall |
| 5,636,643 A | 6/1997 | Argenta et al. |
| 5,645,081 A | 7/1997 | Argenta et al. |
| 5,766,233 A | 6/1998 | Thiberg |
| 5,974,338 A * | 10/1999 | Asano ................ A61B 5/14535 600/322 |
| 5,976,175 A | 11/1999 | Hirano et al. |
| 6,071,267 A | 6/2000 | Zamierowski |
| 6,128,797 A | 10/2000 | Shaffer |
| 6,135,116 A | 10/2000 | Vogel et al. |
| 6,142,982 A | 11/2000 | Hunt et al. |
| 6,159,236 A | 12/2000 | Biel |
| 6,168,591 B1 | 1/2001 | Sinofsky |
| 6,187,029 B1 | 2/2001 | Shapiro et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,350,168 B1 | 2/2002 | Kroll et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,562,013 B1 | 5/2003 | Marasco, Jr. |
| 6,814,079 B2 | 11/2004 | Heaton et al. |
| 6,994,702 B1 | 2/2006 | Johnson |

(56) References Cited

U.S. PATENT DOCUMENTS

| | | | |
|---|---|---|---|
| 7,947,033 | B2 | 5/2011 | Ganapathy et al. |
| 2002/0077661 | A1 | 6/2002 | Saadat |
| 2002/0111537 | A1 | 8/2002 | Taylor et al. |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2003/0187486 | A1 | 10/2003 | Savage et al. |
| 2005/0010270 | A1 | 1/2005 | Laufer |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |

OTHER PUBLICATIONS

Response filed Jun. 11, 2002 for U.S. Appl. No. 09/544,399.
Non-Final Office Action date mailed Jun. 18, 2003 for U.S. Appl. No. 09/544,399.
Response filed Sep. 5, 2003 for U.S. Appl. No. 09/544,399.
Non-Final Office Action date mailed Dec. 17, 2003 for U.S. Appl. No. 09/544,399.
Response filed Jun. 16, 2004 for U.S. Appl. No. 09/544,399.
Final Office Action date mailed Sep. 14, 2004 for U.S. Appl. No. 09/544,399.
Response filed Nov. 5, 2004 for U.S. Appl. No. 09/544,399.
Advisory Action date mailed Nov. 12, 2004 for U.S. Appl. No. 09/544,399.
Notice of Allowance date mailed Dec. 3, 2004 for U.S. Appl. No. 09/544,399.
Supplemental Notice of Allowance date mailed Mar. 10, 2005 for U.S. Appl. No. 09/544,399.
RCE and Amendment filed Apr. 7, 2005 for U.S. Appl. No. 09/544,399.
Notice of Allowance date mailed Jun. 24, 2005 for U.S. Appl. No. 09/544,399.
Supplemental Notice of Allowance date mailed Jul. 21, 2005 for U.S. Appl. No. 09/544,399.
Restriction Requirement date mailed Apr. 8, 2010 for U.S. Appl. No. 11/327,662.
Response filed May 4, 2010 to Restriction Requirement for U.S. Appl. No. 11/327,662.
Non-Final Office Action date mailed Aug. 11, 2010 for U.S. Appl. No. 11/327,662.
Response filed Oct. 15, 2010 for U.S. Appl. No. 11/327,662.
Final Office Action date mailed Dec. 13, 2010 for U.S. Appl. No. 11/327,662.
Response filed Jan. 13, 2011 for U.S. Appl. No. 11/327,662.
Notice of Allowance date mailed Jan. 31, 2011 for U.S. Appl. No. 11/327,662.
N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96.
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61(1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.

(56) References Cited

OTHER PUBLICATIONS

Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164.
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," *British Journal of Surgery* 73(1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax," *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007.)

\* cited by examiner

SYSTEMS AND METHODS FOR DETECTION OF WOUND FLUID BLOOD AND APPLICATION OF PHOTOTHERAPY IN CONJUNCTION WITH REDUCED PRESSURE WOUND TREATMENT SYSTEM

CROSS-REFERENCE TO RELATED APPLICATIONS

This application is a continuation of U.S. patent application Ser. No. 11/327,662, filed on Jan. 6, 2006 now U.S. Pat. No. 7,947,033, which is a continuation of U.S. patent application Ser. No. 10/867,990, filed on Jun. 15, 2004, now U.S. Pat. No. 7,524,286, which is a continuation-in-part of U.S. patent application Ser. No. 10/085,321, filed on Feb. 28, 2002, now U.S. Pat. No. 6,856,821, which is a continuation-in-part of U.S. patent application Ser. No. 09/579,755, filed on May 26, 2000, now abandoned; the present application is also a continuation-in-part of U.S. patent application Ser. No. 09/544,399, filed on Apr. 6, 2000, now U.S. Pat. No. 6,994,702, which claims the benefit of U.S. Provisional Patent Application No. 60/127,936, filed on Apr. 6, 1999; and the present application is also a continuation-in-part of U.S. patent application Ser. No. 10/090,358, filed on Mar. 4, 2002, now U.S. Pat. No. 7,799,004, which claims the benefit of U.S. Provisional Patent Application No. 60/273,587, filed on Mar. 5, 2001, all of which are hereby incorporated by reference.

BACKGROUND OF THE INVENTION

1. Field of the Invention

The present invention relates to generally to optical systems and methods for detecting the presence of blood in fluids derived from the body. The present invention relates more specifically to a wound fluid blood detection device and method for use in conjunction with reduced pressure wound treatment (RPWT) systems and related systems. The detection device is operable to provide a notification signal to a health care provider and/or the patient of the presence of wound fluid with excess blood and/or is operable to modify or cease the reduced pressure wound treatment.

2. Description of the Related Art

General Background on Wound Treatment

Various therapies have been developed over time to facilitate the process of wound closure and healing. Wound closure generally involves the inward migration of epithelial and subcutaneous tissue adjacent the wound. This migration is ordinarily assisted by the inflammatory process, whereby blood flow is increased and various functional cell types are activated. Through the inflammatory process, blood flow through damaged or broken vessels is stopped by capillary level occlusion, where after cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound.

Without sufficient blood flow, the epithelial and subcutaneous tissues surrounding the wound not only receive diminished oxygen and nutrients, but are also less able to successfully fight bacterial infection and thus are less able to naturally close the wound. Until recently, such difficult wounds were addressed only through the use of sutures or staples. Although still widely practiced and often effective, such mechanical closure techniques suffer a major disadvantage in that they produce tension on the skin tissue adjacent the wound. In particular, the tensile force required in order to achieve closure using sutures or staples causes very high localized stresses at the suture or staple insertion point. These stresses commonly result in the rupture of the tissue at the insertion points, which can eventually cause wound dehiscence and additional tissue loss.

Additionally, some wounds harden and inflame to such a degree due to infection that closure by stapling or suturing is not feasible. Wounds not reparable by suturing or stapling often require prolonged hospitalization, with its attendant high cost, and major surgical procedures, such as grafts of surrounding tissues. Examples of wounds not readily treatable with staples or suturing include large, deep, open wounds; decubitus ulcers; ulcers resulting from chronic osteomyelitis; and partial thickness burns that subsequently develop into full thickness burns.

As a result of these and other shortcomings of mechanical closure devices, methods and apparatus for draining wounds by applying continuous reduced pressures have been developed. When applied over a sufficient area of the wound, such reduced pressures have been found to promote the migration of epithelial and subcutaneous tissues toward the wound. In practice, the application to a wound of reduced gauge pressure, commercialized by Applicant under a number of different reduced pressure wound treatment (RPWT) systems, typically involves the mechanical-like contraction of the wound with simultaneous removal of excess fluid. In this manner, RPWT augments the body's natural inflammatory process while alleviating many of the known intrinsic side effects, such as the production of edema caused by increased blood flow absent the necessary vascular structure for proper venous return.

Vacuum or reduced pressure induced healing of open wounds has recently been popularized by Kinetic Concepts, Inc. of San Antonio, Tex., through its commercially available RPWT systems product line. The reduced pressure induced healing process has been described in commonly assigned U.S. Pat. No. 4,969,880, issued on Nov. 13, 1990 to Zamierowski, as well as in its related patents, including U.S. Pat. No. 5,100,396, issued on Mar. 31, 1992; U.S. Pat. No. 5,261,893, issued on Nov. 16, 1993; and U.S. Pat. No. 5,527,293 issued Jun. 18, 1996, the disclosures of which are each incorporated herein by reference. Further improvements and modifications of the RPWT process are also described in U.S. Pat. No. 6,071,267, issued on Jun. 6, 2000 to Zamierowski and U.S. Pat. Nos. 5,636,643 and 5,645,081 issued to Argenta et al. on Jun. 10, 1997 and Jul. 8, 1997 respectively, the disclosures of which are each incorporated by reference as though fully set forth herein. Additional improvements have also been described in U.S. Pat. No. 6,142,982, issued on May 13, 1998 to Hunt, et al.

While RPWT has been highly successful in the promotion of wound closure, healing many wounds previously thought largely untreatable, some difficulties remain. Because the very nature of RPWT dictates an atmospherically sealed wound site, the therapy must often be performed to the exclusion of other beneficial and therefore desirable, wound treatment modalities and wound monitoring processes. Two such monitoring processes addressed in the present disclosure include wound fluid blood detection and blood gas monitoring. One such treatment modality addressed in the present disclosure is phototherapy—a method for wound treatment wherein appropriate wavelengths of light are directed into or about the wound bed.

Wound Fluid Blood Detection

Processes for analyzing the composition of fluids from the body are generally well developed in the art as long as the fluid may be removed as an in-vitro sample and analyzed remote from the patient. Various spectral absorption measurement techniques may be applied to body fluids to determine their composition and content. In particular, near infrared spectroscopy and optical detection have been used in the past in oximetry measurements associated with blood fluids. Colorimetric oximetry systems monitor the $O_2$ saturation percentage in blood by comparing absorption in a red spectral band to absorption saturation at the isosbestic point of hemoglobin and deoxyhemoglobin and are typically employed in co-oximeters and cardiac bypass pump circuits. Photometric detection of hemoglobin has been accurately used for calculating the hematocrit levels at multiple ($\geq 3$) wavelengths at 570 nm, 640 nm and 805 nm typically in blood. These methods require removal of blood fluids from the body. Pulse oximetry methods allow for saturation measurements in-vivo but reliable hematocrit measurements have proven to be problematic due to scattering entities in whole anatomy such as skin and bone.

There are currently no devices, however, that perform real-time in-vivo blood detection monitoring, or blood detection in wound fluids as such fluids exist in direct association, or near direct association with the wound site Hematocrit and $O_2$ saturation levels have been measured (Abbott's $SaO_2$ PA catheter) in-vivo by optical scattering techniques and by colorimetry in whole free flowing blood. The presence of numerous optical components in the blood/wound-fluid mixture, however, generally limits the ability to use scattering based methods for real-time blood detection. Colorimetric based methods, on the other hand, do show some promise for application in conjunction with in-wound or near-wound fluid conduction systems as they are less susceptible to errors generated by non-blood opaque or dark fluid components. The specificity with which certain colorimetric techniques are able to discern the presence of blood in a mixed component fluid makes them, candidates for use in conjunction with in-vivo or near in-vivo detection.

It is therefore a primary object of the present invention to improve over the prior art by providing a system and method for detecting the presence of elevated levels of blood in body fluids in an in-vivo or near in-vivo environment.

It is a further object of the present invention to improve over the prior art by providing a system and method for detecting the presence of elevated levels of blood in wound fluids.

It is a further object of the present invention to improve over the prior art by providing a system and method for detecting the presence of elevated levels of blood in wound fluids while such fluids are present in the wound bed or immediately adjacent the wound bed subsequent to withdrawal from the wound.

It is a further object of the present invention to improve over the prior art by providing a system and method for detecting the presence of elevated levels of blood in wound fluids operable in conjunction with reduced pressure wound treatment systems.

It is a further object of the present invention to improve over the prior art by providing an additional safety feature for the operation of reduced pressure wound treatment systems through the detection of elevated levels of blood in wound fluids.

It is a further object of the present invention to improve over the prior art by providing a system and method for detecting blood in wound fluids in a manner sufficient to provide timely notification to a health care provider or the patient as to the existence of the elevated blood level condition.

It is a further object of the present invention to improve over the prior art by providing a system and method for detecting blood in wound fluids, operable in conjunction with a reduced pressure wound treatment system, and capable of providing timely modification or cessation of the reduced pressure wound treatment upon the detection and/or measurement of an elevated blood level condition.

It is still a further object of the present invention to provide a system and method for detecting the presence of blood in wound fluids without the need for additional invasive components being positioned within the wound bed or within the wound bed dressing.

It is still a further object of the present invention to provide a system and method for the detection of blood, in wound fluids operable in conjunction with a non-invasive blood gas monitoring device and a cooperative reduced pressure wound treatment system.

It is still a further object of the present invention to provide a system and method for the detection of blood in wound fluids operable in conjunction with a system for measuring wound dressing pressures and a cooperative reduced pressure wound treatment system.

It is still a further object of the present invention to provide a system and method for the detection of blood in wound fluids operable in conjunction with a reduced pressure wound treatment system, having functional components that additionally or alternately operate to provide phototherapy to the wound.

Finally, it is still a further object of the present invention to improve over the prior art by providing a method and apparatus for the detection of blood in wound fluids drawn into a reduced pressure wound treatment system that may be implemented in conjunction with the reduced pressure wound treatment system without the need for modification or interruption of the system.

SUMMARY OF THE INVENTION

In fulfillment of these and other objectives, the present invention provides wound fluid blood detection systems and methods operable in conjunction with reduced pressure wound treatment (RPWT) systems, as well as additional ancillary therapy and monitoring systems applied with RPWT systems. The blood detection monitor operates by optically characterizing the content of wound fluids to the extent of identifying a percentage blood content in the fluids. The optical identification relies upon the transmission of select wavelengths of light across a volume of wound fluid to a photo detector system capable of quantifying the absorption characteristics of the fluid at the select wavelengths. The use of at least two discreet wavelength ranges associated with characterizing hemoglobin in blood, allows for the identification and discrimination of blood content from other opaque materials present in the wound fluid. Light emitting diodes configured to provide illumination in the specified wavelengths are directed across a volume of wound fluid toward a photo detector, also configured to be sensitive in the select wavelengths. Blood that is present in the wound fluid absorbs light in the select wavelength ranges, which absorption can be measured (and quantified by reference to a calibrated norm) to identify an increased level of blood present in the wound fluid.

A variety of locations for establishing the optical monitoring arrangement are provided for, each different from the other, but each consistent in its geometry and function during use in conjunction with a RPWT system to facilitate the healing of a wound. The optical detection systems are implemented in conjunction with either a fluid flow conduit associated with drainage from the wound (i.e. the reduced pressure tubing directed away from the wound dressing) or more directly in association with the materials that comprise the wound dressing positioned within the wound bed itself. In addition, the optical detection arrangement may be direct as between the LEDs and the photo detector, or may be indirect as conducted by fiber optics from LEDs at a remote location to the monitoring location and then back again to a remotely positioned photo detector.

In addition, the present invention is configured to operate in conjunction, not only with the components present in typical RPWT systems, but also with the system components present in blood gas monitoring systems such as those described in the parent application identified above.

As a further feature of the present application, the systems appropriate for implementation of the specific wavelength illumination of the wound fluids, and in one preferred embodiment, of the wound bed itself, lend themselves to use in conjunction with illumination in discreet light wavelengths suitable for the application of phototherapy to the wound bed.

The primary objective of the present invention is to develop an optical technique to detect blood in wound fluids while applying RPWT during the wound healing process and thereby detect hemorrhage events in the wounds. The primary action within this concept is to identify the spectral properties of blood and use these properties as the basis for an algorithm for quantifying a percentage blood content and for determining when such content is above an acceptable level such that notification to a healthcare provider or the patient and/or modification of the RPWT can be effected.

RPWT may be implemented in conjunction with a variety of wound conditions and wound types. In addition, such therapy may be initiated at different stages during the healing process. Although the level of reduced pressure typically associated with such therapies is not extreme (i.e. the level of reduced pressure is seldom in the range that would cause disruption of tissue, even in the delicate wound bed environment) the presence of an open blood vessel within the wound could result in excessive flow of blood facilitated by the reduced pressure. RPWT is typically contraindicated when a wound is actively bleeding and instructions are generally provided to take steps to stop such bleeding before application of the RPWT dressing is made. Despite this cautionary action, any wounds subjected to RPWT remain susceptible to the initiation of bleeding within the wound by way of a number of factors unassociated with the RPWT itself. It is not uncommon, as an example, for a patient to agitate and sufficiently traumatize a wound by mere movement to the point where blood vessels that had previously stopped bleeding are reopened and drain blood into the wound fluids within the wound bed. Once this occurs, the level of reduced pressure typically utilized with RPWT systems may be sufficient to slow or prevent the re-coagulation of blood within a blood vessel as might normally occur. For the above reasons it becomes beneficial to have a system operable in conjunction with RPWT systems to detect the presence of blood in the wound fluids at a point in time when corrective action can be taken.

Two aspects of the present invention lead to integration of the blood detection system described with other valuable ancillary systems previously identified (in the parent applications hereto) as being beneficial and operable in conjunction with RPWT systems. These features include: first, the ability of the present blood detection system to operate in conjunction with the components of a blood gas monitoring system that itself has been configured to operate in conjunction with an RPWT system; and second, the ability of certain components within the present blood detection system to serve a dual function as both a component of the blood detection system and a component of a phototherapy system operable simultaneously with, or in the alternative to, the blood detection system. These aspects also lead to the ability to include pressure responsive elements (sensors) in conjunction with the optical devices to obtain a measure of wound bed pressure at the same time as blood detection occurs.

Finally, many other features, objects and advantages of the present invention will be apparent to those of ordinary skill in the relevant arts, especially in light of the foregoing discussions and the following drawings and exemplary detailed description.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims which may be drawn hereto.

The systems and methods of the present invention as shown in the attached figures employ photometric or optical methods for detecting the presence (and ultimately, the concentration) of blood in wound fluid being drawn away from the wound by Reduced Pressure Wound Treatment (RPWT) devices and systems. In general, LEDs in the 540/560/580/620/640/660 nm and 800 nm ranges are used as the emitters and a photo detector sensitive to the same range of wavelengths is used as the receptor. These solid state optical components are positioned across a flow stream of the wound fluid and measurements are taken of the absorption of the illuminating light in a manner that specifically identifies and quantifies the presence of blood in the fluid. Variations in the system include different structures to hold or contain the wound fluid while optical measurements are being made as well as different placements of the detection site.

One objective common to each implementation of the various embodiments that follow is to allow for either the activation of a caregiver or patient notification signal and/or the automatic modification or cessation of the RPWT. In either case the detection system of the present invention is capable of providing a digital output signal suitable for triggering any of a number of different caregiver/patient notification signaling devices or suitable for modifying the RPWT operation. A notification signal would be associated with the identification of a wound fluid blood content that exceeded a pre-set level (>30% as an example) indicative of an abnormal condition (excessive bleeding) in the wound. Different types of wounds would merit different settings in this regard as would differing stages of wound healing.

Alternately (or in addition) the detection system could generate a staged signal that provided more refined "instructions" to the RPWT system being implemented. For example, a given wound fluid blood concentration level could trigger a reduction in the reduced pressure level of the therapy without altogether ceasing the therapy. A greater concentration or a sudden change in concentration could instead trigger the cessation of the therapy (most likely in conjunction with a notification signal). Because there exists a variety of RPWT regimens, a variety of modifications to these regimens, as triggered by wound fluid blood concentration levels, are anticipated.

Figure 1:
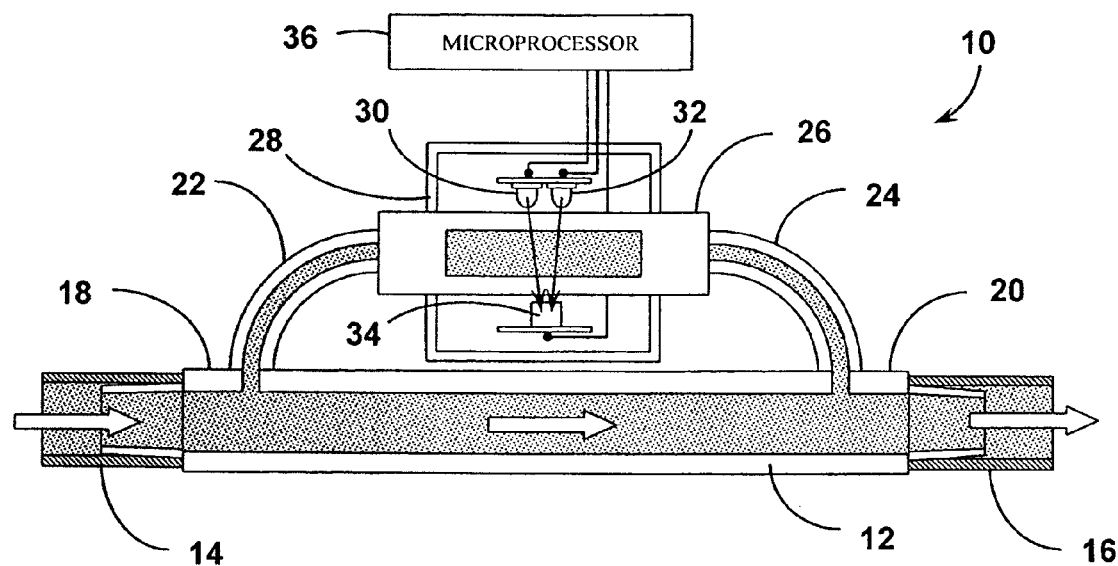
FIG. 1 is a schematic partial cross-sectional view of a first embodiment of the system of the present invention utilizing a cuvette shunt.

FIG. 1 shows the basic components associated with a first implementation of the preferred embodiment of the present invention. In this implementation, blood detector 10 is connected in line with reduced pressure wound treatment (RPWT) tubing to form a shunt for the flow of wound fluids in a manner that allows accurate measurement of the percentage blood content of the wound fluids. Tubing connector 12 has an inlet port 18 that is connected to a section of RPWT tubing 14 that is in turn connected to a typical RPWT dressing port (not shown). An opposite end of tubing connector 12 has an outlet port 20 connected to a continuation of RPWT tubing 16 which connects to the typical reduced pressure fluid collection canister (not shown). Arrows in this view indicate the flow of wound fluids through the system under the influence of the reduced pressure source drawing the fluids away from the wound.

Provided to form a shunt for a portion of the flow of fluid from the main channels are connector tubes 22 and 24. Wound fluid flows into the detector of the system through connector tube 22 and into detection cuvette 26 where the optical components of the system serve to analyze the wound fluid in the manner described in more detail below. From detection cuvette 26 the diverted flow continues into connector tube 24 back into the wound fluid flow stream in tubing connector 12 and from there back into the RPWT tubing 16.

Detection cuvette 26 provides a detection chamber with a known geometry (i.e. a consistent diameter and volume) such that quantitative measurements of the absorption of select wavelengths of light can be made. In the embodiment shown in FIG. 1, two light emitting diodes (LEDs) capable of emitting light in select narrow wavelength bands are positioned on one side of detection cuvette 26 and positioned so as to direct light across the clear containment enclosure of the cuvette. A first LED 30 is, in the preferred embodiment, selected to emit light in the 805 nanometer (nm) wavelength range, while a second LED 32 is configured to emit light in the 542/576/740 nm wavelength range. LEDs with such specifications are readily available in the industry. The light from each of the LEDs is alternately transmitted across detection cuvette 26 to a photo detector 34 positioned opposite the LEDs. Photo detector 34 is sensitive to a full range of wavelengths from 500-850 nm. Again, such electronic devices are readily available in the industry.

LEDs 30 and 32 are driven by appropriate electronic circuitry (not shown but well known in the art) and the output signal from photo detector 34 is likewise amplified, conditioned and processed by the appropriate electronic circuitry (not shown). The output of photo detector 34 is eventually received and analyzed by microprocessor 36, which also serves to control the illumination within the detector by driving LEDs 30 and 32. The entire LED/photo detector system is enclosed in LED enclosure 28 that additionally surrounds cuvette 26 and prevents extraneous light from entering into the detection system. The LEDs in the system may be pulsed sequentially (under the control of microprocessor 36) to effect absorption measurements by photo detector 34. The absorption measured for the 542/576/740 nm and the 805 nm wavelengths of light is then used (according to a reference value calibrated previously in conjunction with the specific cuvette geometry) to estimate the concentration (percentage) of blood in the wound fluid.

Figure 2:
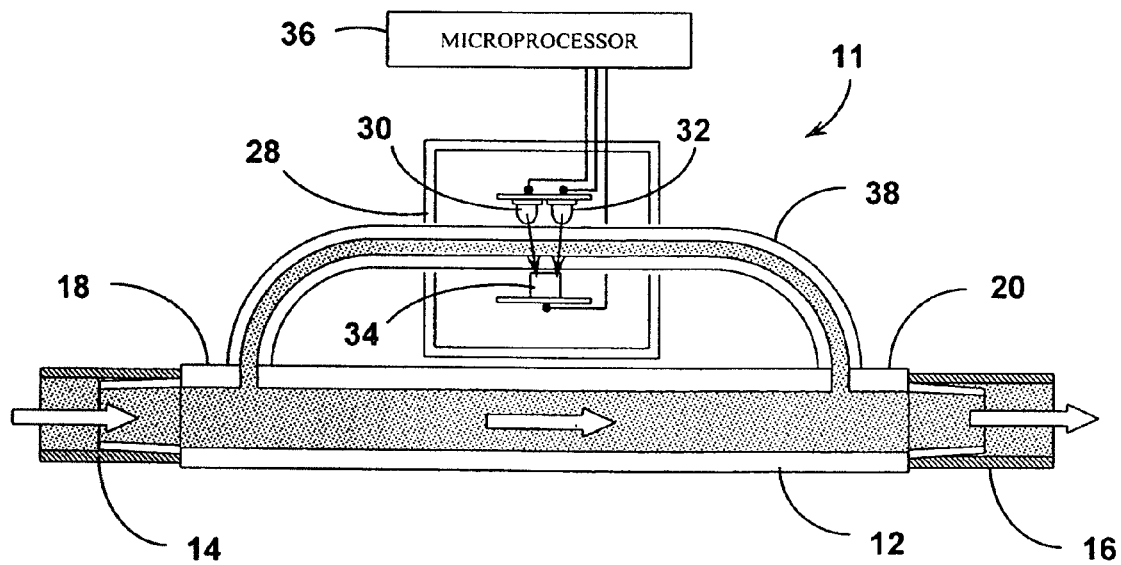
FIG. 2 is a schematic partial cross-sectional view of a second embodiment of the system of the present invention utilizing a silicon tube shunt.

The embodiment shown FIG. 1 makes use of a "laboratory grade" chamber within detection cuvette 26 to measure the light absorption of the wound fluid under consistently precise conditions. Where such precision may not be required, FIG. 2 provides an alternative to the embodiment shown in FIG. 1 wherein the use of a cuvette is dispensed with and a section of clear silicon based tubing 38 is utilized in its place. Clear silicon based tubing 38 can provide adequate light transmission, and further can provide sufficiently consistent geometry, as to permit accurate readings for the same LED/photo detector arrangement shown and described above in conjunction with FIG. 1. The same LED wavelengths and photo detector sensitivities may be utilized with accommodations for the differences in geometry and tubing wall transmission characteristics being made during the calibration and referencing process.

Implementation of the device shown in FIG. 2 would accommodate situations where a variety of different types of RPWT system tubing is in use In order to standardize the geometry and allow for an accurate calibration of the system, tubing of a known structure is used in a shunt off of the primary flow. While the absolute accuracy of such a system may be less than that of the system shown in FIG. 1 the changes in wound fluid blood content remain sufficiently discernable to allow the system to trigger an alarm and/or to modify the RPWT operation as described above.

Figure 3:
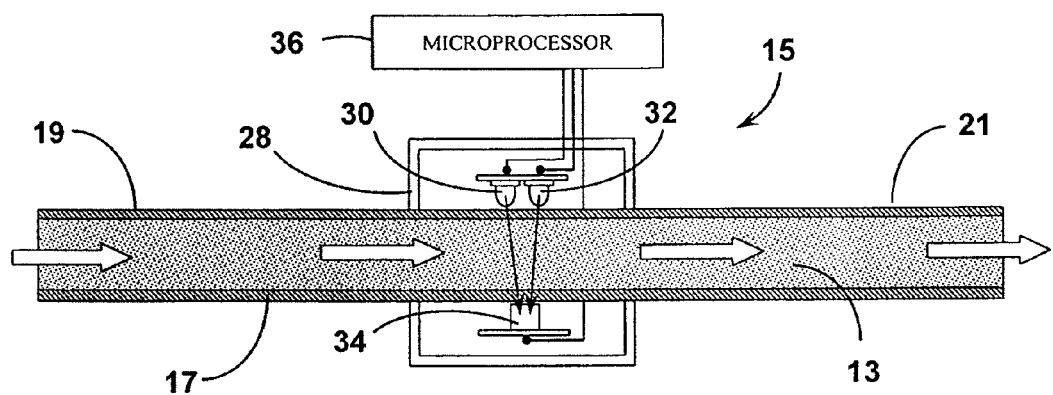
FIG. 3 is a schematic partial cross-sectional view of a third embodiment of the present invention showing its application directly on RPWT tubing.

FIG. 3 discloses a third implementation of a preferred embodiment of the present invention wherein the wound fluid blood detector 15 may be positioned around a section of tubing 17 as might be typically utilized in standard RPWT systems. The flow of wound fluid 13 in this view (again designated by the arrows) is from a first end 19 of tubing section 17 connected to the wound dressing (not shown) through to a second end 21 of tubing section 17 connected to the reduced pressure source (typically through a fluid collection canister) not shown. In the view in FIG. 3, light in the same narrow range of wavelengths from LEDs 30 and 32 is directed through the walls of the tubing 17 and through the flow of wound fluid 13 in the existing reduced pressure system. This light, after partial absorption by the components of the wound fluids, is received by photo detector 34. The same processing and analysis is carried out by microprocessor 36, albeit with algorithms that are tuned and referenced to recognize the specific attenuation and dispersive effects of the walls of the RPWT tubing.

The arrangement shown in FIG. 3 may, in the preferred embodiment, be implemented using a cylindrical "clamshell" structure for LED enclosure 28. In this manner the device may be positioned and secured to any of a number of locations on the tubing either adjacent or distant from the wound itself. The low voltage/low current connections to the microprocessor may be structured with anything from a simple electrical conductor bundle that would follow the RPWT system tubing up to the balance of the "remote" equipment (reduced pressure source, etc.). In the alternative, the low power electronics (LEDs and photo detector) of the device could be locally powered (as by an onboard battery) and a wireless signal communication could be structured between the detector device (acting essentially as a remote blood sensor) and the signal processing instrumentation containing the microprocessor.

Figure 4:
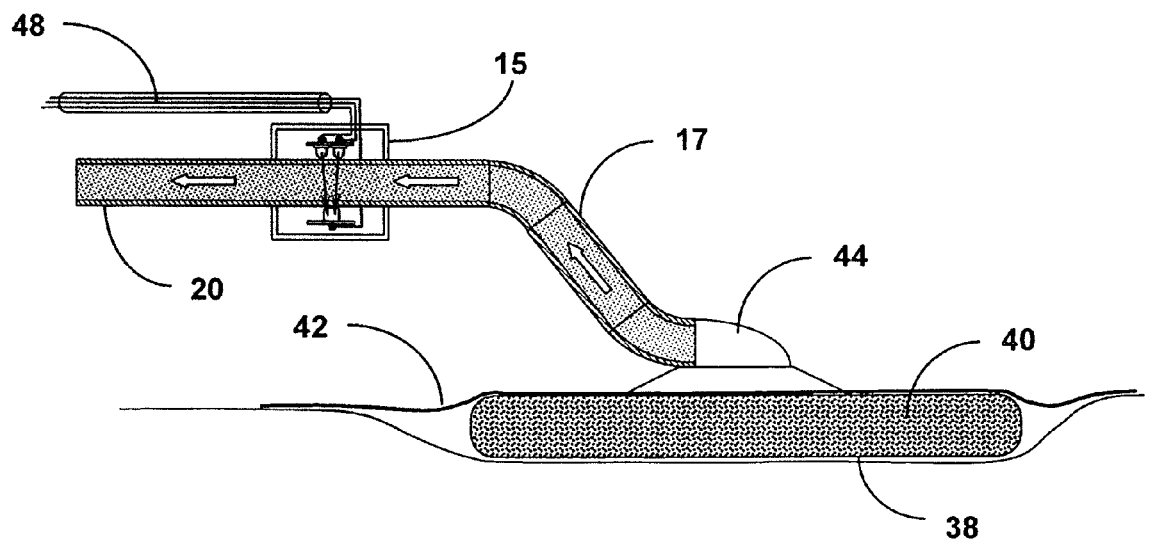
FIG. 4 is a cross-sectional view of an application of the embodiment shown in FIG. 3 in conjunction with an RPWT wound dressing.

FIG. 4 shows the device represented in detail in FIG. 3 as implemented in conjunction with a RPWT dressing. In this view, blood detector 15 is connected by way of signal wires 48 to a microprocessor based signal conditioning system (not shown) as described above. RPWT tubing 17 is connected to wound dressing vacuum port 44 positioned as is known in the art in conjunction with porous foam dressing 40 positioned in wound bed 38. An adhesive impermeable drape 42 is positioned over porous foam dressing 40 and seals the dressing within wound bed 38. Vacuum port 44 extends into the enclosed wound bed volume and serves to provide the reduced pressure to the enclosed dressing.

FIG. 4 shows that the device of the present invention may be positioned in close proximity to the wound dressing positioned on the patient in order to detect elevated levels of blood concentration in the wound fluids at the earliest possible point in the system. Depending on the flow rate of the wound fluids in the system (which is dependent on a number of factors including the level of reduced pressure) the presence of abnormal levels of blood in the wound fluid could be delayed by positioning the detection device further from the wound dressing. The following further embodiments of the present invention integrate the detection device into the wound dressing itself and further expand the functionality of the device to include phototherapy capabilities.

Figure 5:
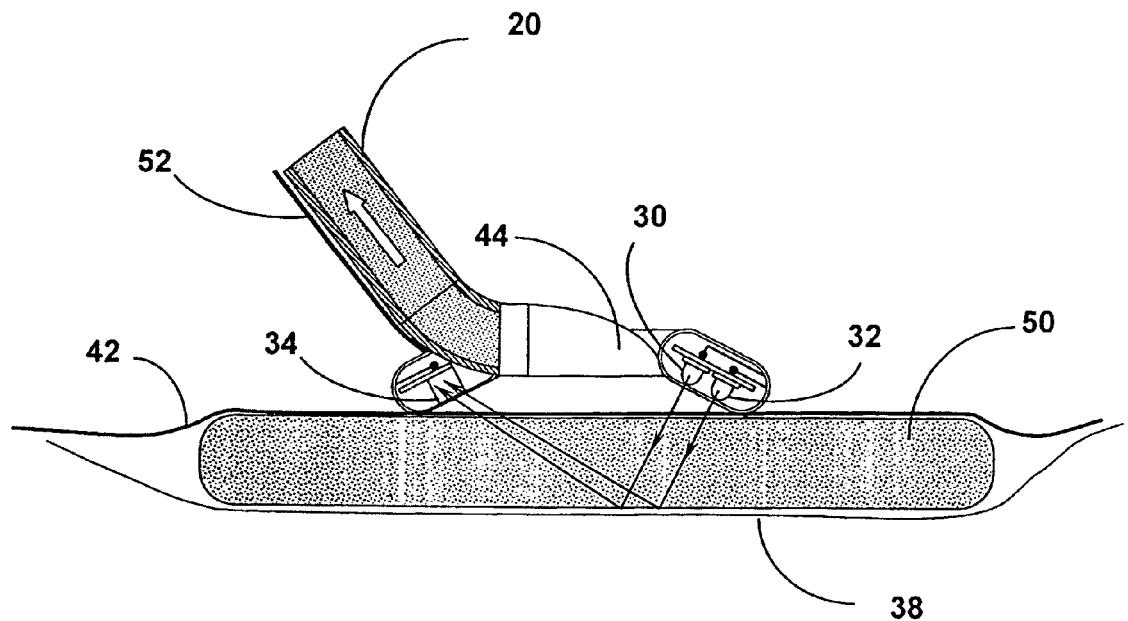
FIG. 5 is a detailed cross-sectional view of a further embodiment of the present invention located in conjunction with an RPWT wound dressing.

FIG. 5 shows an alternative preferred embodiment of the present invention wherein the LEDs and photo detector of the system are positioned in direct proximity to the wound bed and the RPWT dressing on the patient. In FIG. 5, wound bed 38 has positioned within it a layer of transparent or translucent porous foam 50, the foam being made of a material capable of transmitting light of the frequencies emitted by LEDs 30 and 32. In the structure shown, light from the LEDs is directed through the clear components of dressing vacuum port 44 into translucent foam 50 at an angle that generally directs it towards an area of the foam where illumination of the foam is detected by photo detector 34. The nature of RPWT is such that the wound fluids are drawn up into foam 50 in a manner that saturates the foam with the wound fluids and thereby allows the detection of blood in the fluids being drawn into the system. Various polymer based fibrous foams are known in the art that may be utilized to provide both the necessary reduced pressure transmission (porosity) and the necessary light transmission qualities required for the present invention. (See the disclosure of the parent application identified above and incorporated herein.) Electrical signal conductor bundle 52 provides the voltage and current required to drive LEDs 30 and 32 as well as the return signal line for the photo detector 34.

Figure 6:
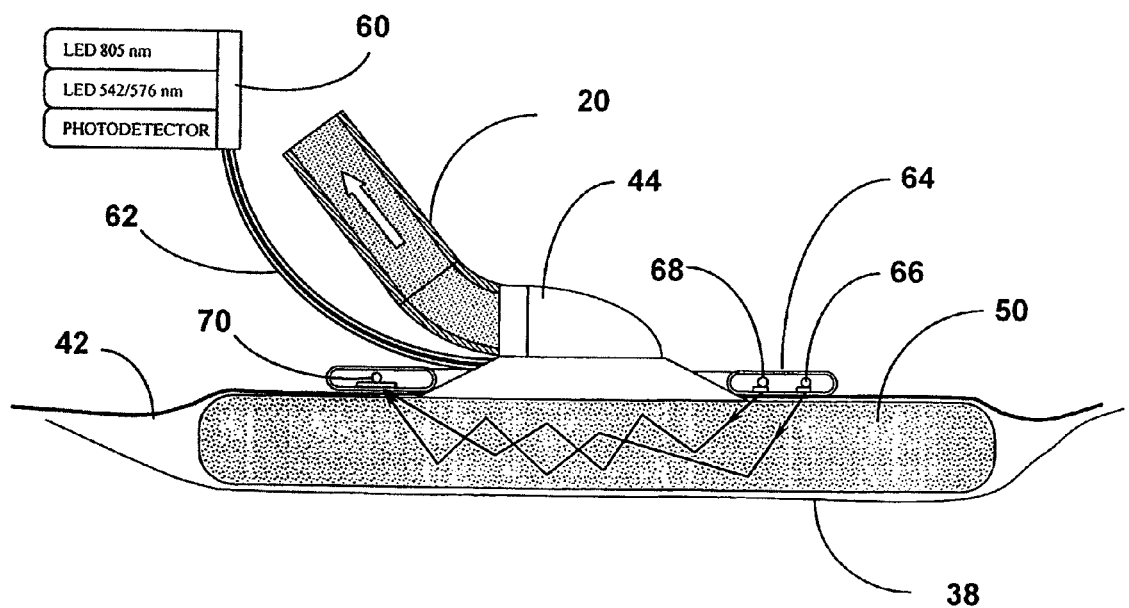
FIG. 6 is a detailed cross-sectional view of a further alternative embodiment of the present invention utilizing fiber optics for illumination and detection within the RPWT wound dressing.

In some instances, it may be undesirable to structure a wound dressing with electrical connectors, even of the low voltage, low current type associated with driving the LEDs and receiving signal data from the photo detector in the present system. In such instances, a further alternative embodiment of the present invention involves conducting the light generated by each of the LEDs and the light to be received by the photo detector, to and from the wound bed at a remote location by way of optical fibers. FIG. 6 shows one such implementation of this embodiment. In this view, remote, circuitry 60 provides the placement of LEDs 30 and 32 as well as the placement of photo detector 34 in a remote location apart from the patient. Optical fiber lines 62 are connected to each of the three discreet devices associated with the operation of the system of the present invention. Fiber optic cable 62 connects remote circuitry 60 by way of light channels to appropriate fiber optic terminal light ports positioned more directly in association with the RPWT dressing, and may also include the necessary connections for direct measurement of wound dressing pressures.

Associated with vacuum port 44 is an illumination ring 64 positioned in close proximity to adhesive drape 42 (which in the preferred embodiment is typically transparent) positioned over translucent porous foam 50. The fiber optic lines provide the necessary illumination source for fiber optic ports that effectively function in the manner of the LEDs and the photo detector to transmit and receive light waves into and from the wound fluid saturated foam within the dressing. Fiber optic port 66, for example, provides light at a wavelength associated with LED 32 while fiber optic port 68 provides light of a wavelength associated with LED 30. In similar fashion, fiber optic port 70 collects the light scattered (and partially absorbed) by the wound fluids within translucent foam 50 and directs it by fiber optic cable 62 up to photo detector 34.

The arrangement shown in FIG. 6 utilizes separate optic lines for the two discrete LEDs providing light of the indicated discrete wavelengths. Those skilled in the art will recognize, however, that a single optic wave guide (optic fiber) could be used and switched between the two LEDs as needed. In the preferred embodiment, fiber optic ports 66 and 68 may simply be two of an array of ports all connected to the same source (at a particular instant in time). In this manner a greater illumination of the wound bed might be achieved. In addition, the phototherapy aspects of the present invention, discussed in more detail below, may be more easily implemented with this multiple source—single optic fiber arrangement. Under the processor control of the system of the present invention, the wound bed might be illuminated in one instant with light of the first LED wavelength (805 nm) followed by light in the next instant of the second LED wavelengths (540/576/740 nm) followed by light in a subsequent period of time in a wavelength spectrum appropriate for phototherapy. Illumination ring 64 may also include the necessary sensors for returning temperature and/or pressure measurements of the wound bed.

The fiber optic connections shown in FIG. 6 may be loosely associated with the tubing connecting the RPWT dressing to the reduced pressure source or they may be integrated into the tubing utilized in the reduced pressure wound treatment system in the manner described in more detail below. Further, the illumination ring 64 shown in the embodiment of FIG. 6 may be integrally constructed with dressing vacuum port 44 or may be configured as an attachable ring that surrounds or sits adjacent to the port. The association with vacuum port 44 is two-fold, first to centrally position both the illumination and the reception of light waves within the boundaries of the wound dressing and second to provide an existing connecting line (the tubing) with which to direct the fiber optic bundle away from the wound.

Figure 7:
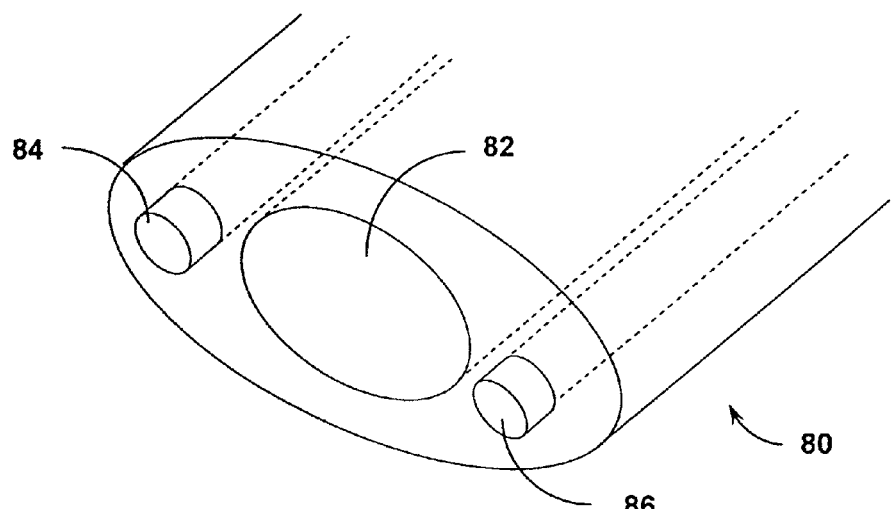
FIG. 7 is a perspective cut away view of a section of tubing appropriate for use in conjunction with the alternative body of the present embodiment of the present invention shown in FIG. 6.

An alternative to the external placement of optical fiber 62 shown in FIG. 6 is a structure wherein the optical fibers are incorporated into the walls of RPWT tubing 80 as disclosed in FIG. 7. This manner of placement eliminates the need for an additional line connecting to the patient and integrates the optical system fully into the structure of the dressing vacuum port 44.

FIG. 7 shows a perspective partial cross-sectional view of a section of RPWT tubing with integrated fiber optic signal lines. The view in FIG. 7 shows tubing with an oval cross-section to accommodate the additional conductors on either side of the primary lumen although tubing of circular (or other geometric) cross section and adequate diameter overall may likewise be suitable for the purposes of the present invention. In this view, tubing 80 is comprised of primary vacuum lumen 82 and two associated fiber optic light conductors 84 and 86. Fiber optic conductor 84 comprises the illuminating light associated with the wavelengths generated by the LEDs as described above. Fiber optic conductor 86 comprises the return line from the detection port to the photo detector. Appropriate terminal connections for the integrated fiber optic wave guides are positioned in conjunction with the LEDs and the photo detector as described and shown in FIG. 6. In addition the fiber optic lines terminate in the dressing vacuum port directly into the fiber optic ports positioned in the illumination ring over the wound dressing. Such terminals and connectors associated with fiber optic signal lines appropriate for use in conjunction with the system of the present invention are well known in the art.

Figure 8:
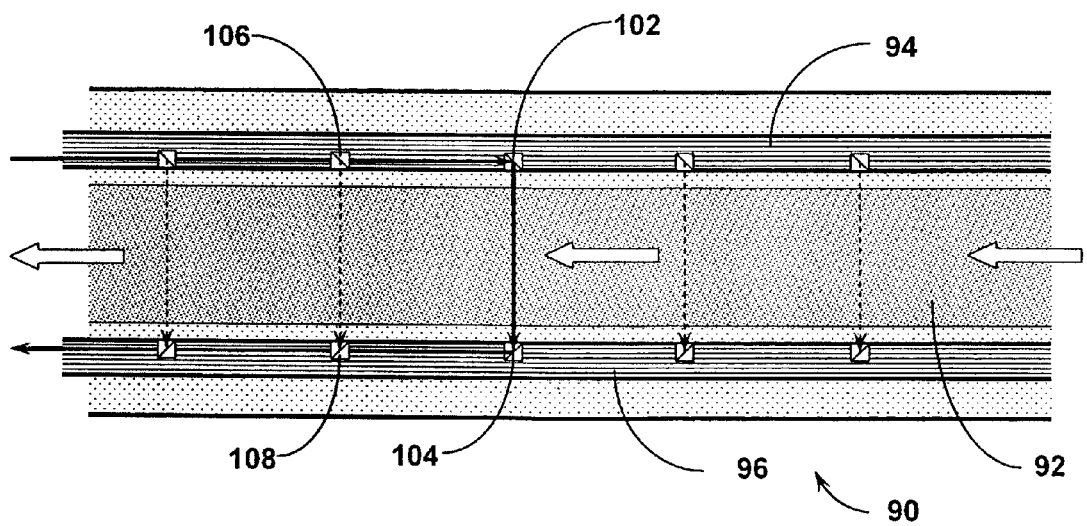
FIG. 8 is a longitudinal cross-sectional view of RPWT tubing further modified to provide yet another alternative embodiment of the present invention.

The structure of RPWT tubing shown in FIG. 7 is directed to communicating light waves to and from the wound dressing where, in conjunction with the translucent foam positioned within the wound bed, a measurement of the absorption properties of the wound fluid can be made. A similar but functionally distinct structure may be utilized in conjunction with the system of the present invention where the measured wound fluid is again associated with the RPWT tubing instead of the wound bed. Reference is made to FIG. 8 for a longitudinal cross-section of a further alternate tubing structure for use in conjunction with the present invention. The tubing shown in FIG. 8 is configured to integrate the blood detection system directly into the walls of a section of the tubing 90 associated with the RPWT system. In this view, a primary lumen 92 is shown wherein wound fluids are transported (by means of reduced pressure) from the wound dressing to the RPWT collection canister. On either side of this primary lumen 92 are specially configured optical fiber bundles 94 and 96 that connect individual optical fibers to individual optical ports positioned along the length of the tubing. On one side of the tubing 90, these ports 102 and 106 (as examples) serve as illumination points directing light at the select wavelengths across the primary lumen 92 (and therefore across the flow of wound fluid) to the opposite side of the tubing 90. In the fiber optic bundle 96 on the opposite side of the tubing 90 are arrayed a number of optical reception ports 104 and 108 (as examples) aligned with the transmission ports 102 and 106, and which are each connected by return fiber optic lines to the photo detector of the system of the present invention.

The structure shown in FIG. 8 integrates an array of illuminating optical ports positioned opposite an array of receiving optical ports within the structure of the RPWT tubing connecting the wound dressing to the reduced pressure source. This structure is a preferred embodiment because of its known geometry and the ability of the system to discriminate between discrete locations along the length of the tubing. By isolating the absorption measurement to a specific set of optical ports additional important information can be acquired regarding the condition of the system at a particular point along the length of the tubing. Each of the transmission optical ports is associated with a direct optical fiber that is "addressable" by the electronics associated with the LED light sources. While the photo detector could likewise be switched to a specific optical fiber/optical port combination, the system and method of measurement are operable by simply switching the transmission line to a known optical fiber/optical port combination and maintaining a single optical fiber connection to the reception ports as a whole. Monitoring of individual port pairs would allow for measurement of the location or speed (or both) of blood containing fluid boluses within the primary lumen.

The array structure disclosed in FIG. 8 allows individual locations along the tubing to be identified, and from this information, a flow characteristic of the wound fluid may also be derived. Therefore, in addition to the ability to detect the presence of blood in the wound fluids that pass a particular point in the tubing, the system is capable of analyzing patterns in light absorption and identifying flow rates as a result. In other words, patterned (sequential) responses to high absorption rates would indicate the passage of a quantity of fluid of a particular character past multiple points in the system, which would provide the basis for measurements of volume and flow rates. Such measurement could factor into a decision regarding the urgency of a bleeding condition within the wound and help dictate the nature of a system response to elevated wound fluid blood content.

Although the present invention finds particular application in conjunction with RPWT systems, there are other fields where the systems and methods of the present invention can likewise be applied. The system could, for example, be used for the purpose of detecting blood in urine, especially in catheterized patients. Likewise the systems and methods could be applied to hemodialysis systems where the blood can be monitored continuously during dialysis. In general, the method can be applied to any mixture of unknown blood and body fluids where a controlled geometry can be established for the illuminated volume of fluid. Such conditions are typically present whenever fluids are being drained from, or circulated from, the body through translucent or transparent conductors. Other applications further include the detection of clots in the above described systems.

Phototherapy Application

As indicated above, it is known that certain regimens of exposing wound beds to electromagnetic waves of specific wavelengths can have beneficial effects on the healing process. The structures of the system of the present invention described above lend themselves to the concurrent application of such phototherapy regimens. The disclosure of parent application (U.S. application Ser. No. 09/544,399, filed Apr. 6, 2000), the complete disclosure of which is incorporated herein by reference, identifies and describes this therapy and the wavelengths of light beneficial to the wound healing process.

In each of the embodiments described above that direct illuminating light into the wound bed (those systems shown in FIGS. 5 and 6 primarily) the LED light sources could easily be configured to operate at the wavelengths suitable for application of the phototherapy regimens. Whether as ancillary LEDs positioned directly above the wound bed (as shown in FIG. 5) or as remotely positioned light sources in light wave communication with the wound bed by fiber optic lines, the systems described above could easily function (in addition or in the alternative) as phototherapy systems. Modification of the wavelength specifications for the LEDs and of the synchronization programming for the control of the LEDs would be all that is required to implement such a system. The same structures, again with specific wavelengths, could also provide a system implementing antimicrobial light application.

Blood Gas Monitoring

As indicated above, it is known to provide systems for blood gas monitoring in conjunction with RPWT systems. The structures of the system of the present invention described above lend themselves to application in association with such blood gas monitoring systems to the extent that they also utilize conduits that carry wound fluids away from the wound bed. The disclosure of the additional parent application (U.S. application Ser. No. 10/867,990, filed Jun. 15, 2004), the complete disclosure of which is incorporated herein by reference, identifies and describes such blood gas monitoring systems and the structures therein that lend themselves to application of the additional blood detection system described hereinabove.

A number of locations within the RPWT system that provide access to fluids to the blood gas monitors are appropriate for placement of the inter-tubular embodiments of the present blood detection system. Whether integrating cuvette elements (FIG. 1), shunt tubes (FIG. 2), or directly connected to the blood gas monitoring tubes (as in FIGS. 3 and 4 herein), the detection system and method may be appropriately applied. Wherever the detection device is placed in conjunction with the RPWT tubing in the present invention, it might easily be placed in similar fashion with blood gas monitoring components in place.

As a further alternate application of the system of the present invention, color responsive chemical sensors (Elisa or non-layered biosensors, for example) may be incorporated in any of the sensing methods described to monitor chemical species in the wound fluid. Such species might include cytokines, creatinine, urea, among other chemicals of interest to those clinicians guiding the normal healing process of the wound.

Although the present invention has been described in terms of the foregoing preferred embodiments, this description has been provided by way of explanation only, and is not intended to be construed as a limitation of the invention. Those skilled in the art will recognize modifications of the present invention that might accommodate specific patient and wound healing environments. Such modifications as to size, spectral wavelengths, illumination intensity, and even system configuration, where such modifications are merely coincidental to the type of wound or to the type of therapy being applied, do not necessarily depart from the spirit and scope of the invention.

We claim:

1. A blood detection system operable with a reduced pressure wound treatment (RPWT) system including a conduit for conducting reduced pressure to a wound dressing and withdrawing wound fluid from a wound, comprising:

an electromagnetic (EM) wave source oriented to at least partially illuminate an interior portion of the conduit, wherein wound fluid is present within the conduit during operation of the RPWT system;

wherein said EM wave source comprises at least one light wave guide integrated into the conduit walls, the light wave guide having a first end oriented to at least partially illuminate the interior portion of the conduit and a second end for receiving EM waves originating adjacent at least one LED remote from the conduit; and an electromagnetic (EM) wave detector positioned to be receptive of attenuated EM waves originating from said source and attenuated after passing through the interior portion of the conduit, said attenuation resulting from a partial and wavelength-specific absorption measurable and indicative of a level of blood within said wound fluid;

wherein said EM wave detector comprises a light wave guide integrated into the conduit walls, the light wave guide having a first end positioned generally opposite of said EM wave source for receiving attenuated EM waves, and a second end for transmitting the attenuated EM waves and terminating adjacent a solid state photo detector remote from the conduit.

2. The blood detection system of claim 1 further comprising
a microprocessor electrically coupled to the EM wave source and the EM wave detector and operable to sequentially pulse the EM wave source to effect absorption by the wound fluid and attenuation measurements by the EM wave detector configured to provide attenuation measurements to the microprocessor, wherein the microprocessor provides an output signal indicating the level of blood within the wound fluid flowing through the conduit.

3. The blood detection system of claim 2, further comprising an alert indicator device, said microprocessor further in signal communication with said alert indicator device and programmed to trigger said alert indicator device upon said signal data indicating a new level of EM wave absorption outside a predetermined range.

4. The blood detection system of claim 2, further comprising an RPWT control device, said microprocessor further in signal communication with said RPWT control device and programmed to operate said RPWT control device upon said signal data indicating a level of EM wave absorption outside a predetermined range, said RPWT control device connected to said RPWT system and serving to modify the operation of said RPWT system.

5. The blood detection system of claim 1, wherein said EM wave source comprises a plurality of light sources, each light source configured to illuminate the wound fluid in a distinct range of spectral wavelengths.

6. The blood detection system of claim 5, wherein the distinct range of spectral wavelengths is selected from a group of wavelengths of 540 nm, 560 nm, 580 nm, 620 nm, 640 nm, 660 nm, and 800 nm.

7. The blood detection system of claim 1, wherein said at least one LED comprises a first LED structured to emit light at a wavelength selected from the group of wavelengths of 542 nm, 576 nm and 740 nm, and a second LED structured to emit light at a wavelength in a range from 800 nm to 810 nm, and said photo detector is sensitive to light at the wavelengths associated with said first and second LEDs.

8. The fluid detection system of claim 1, wherein said EM wave source and said EM wave detector are positioned opposite each other across a diameter of the conduit of the RPWT system.

9. The blood detection system of claim 1, wherein said EM wave source is alternately operable to provide EM wave illumination suitable for absorption by blood components within the wound fluid and operable to provide EM wave illumination suitable for providing phototherapy to a wound undergoing the RPWT.

10. The blood detection system of claim 9, wherein said EM wave illumination suitable for providing phototherapy comprises ultraviolet light.

11. The blood detection system of claim 9, wherein said EM wave illumination suitable for providing phototherapy comprises infrared light.

\* \* \* \* \*